US008859278B2

(12) United States Patent
Trakht et al.

(10) Patent No.: US 8,859,278 B2
(45) Date of Patent: Oct. 14, 2014

(54) FULLY HUMAN HYBRIDOMA FUSION PARTNER CELL LINES

(75) Inventors: Ilya Trakht, Bronx, NY (US); Gavreel Kalantarov, Fort Lee, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 166 days.

(21) Appl. No.: 11/510,490

(22) Filed: Aug. 25, 2006

(65) Prior Publication Data

US 2007/0141064 A1  Jun. 21, 2007

Related U.S. Application Data

(60) Provisional application No. 60/711,819, filed on Aug. 26, 2005.

(51) Int. Cl.
| | |
|---|---|
| *C12N 5/0781* | (2010.01) |
| *C12N 5/09* | (2010.01) |
| *C12N 5/10* | (2006.01) |
| *C07K 16/00* | (2006.01) |
| *C12N 5/16* | (2006.01) |

(52) U.S. Cl.
CPC ............... *C12N 5/163* (2013.01); *C07K 16/00* (2013.01); *C07K 2317/21* (2013.01)
USPC ........ 435/325; 435/346; 435/375; 435/70.21; 435/440; 435/2; 435/455; 436/548

(58) Field of Classification Search
None
See application file for complete search history.

(56) References Cited

U.S. PATENT DOCUMENTS

| 5,521,085 A * | 5/1996 | Fukuda et al. ................. 435/340 |
| 6,197,582 B1 | 3/2001 | Trakht |
| 2005/0095243 A1 | 5/2005 | Chan et al. |

FOREIGN PATENT DOCUMENTS

| EP | 0 044 722 A1 | 1/1982 |
| WO | WO 96/27004 A1 | 9/1996 |

OTHER PUBLICATIONS

Karpas et al., PNAS , 98:1799-1804, 2001.*
Pickering et al., A Human Myeloma Cell Line That Does Not Express Immunoglobulin But Yields a High Frequency of Antibody-Secreting Hybridomas, The Journal of Immunology, 129:406-412, 1982.*
Vaisbourd, M., et al., Hybridoma and Hybridomics, vol. 20, No. 5, 2001, pp. 287-292.
Kalantarov G, Rudchenko S, Trakht I, Human Antibodies, 11, 3, 2002, pp. 85-96.
Gustafsson, B. et al., "SPAM-8, a mouse-human heteromyeloma fusion partner in the production of human monoclonal anitbodies. Establishment of a human monoclonal antibody against cytomegalovirus", IOS Press, NL, vol. 2, No. 1, Jan. 1, 1991, pp. 26-32, XP009114259.
Kalantarov G.F., et al., "Development of a Fusion Partner Cell Line for Efficient Production of Human Monoclonal Anitbodies from Peripheral Blood Lymphocytes", Human Anitbodies, IOS Press, Amsterdam, NL, vol. 11, Jan. 1, 2002, pp. 85-96, XP008032333.
Karpas, A. et al., "A human myeloma cell line suitable for the generation of human monoclonal anitbodies", Proceedings of the National Academy of Science, Washington, DC, US, vol. 98, No. 4, Feb. 13, 2001, pp. 179-1804, XP002179323.

* cited by examiner

*Primary Examiner* — Ronald Schwadron
(74) *Attorney, Agent, or Firm* — Evans & Molinelli PLLC; Judith Evans

(57) ABSTRACT

Certain aspects of the present invention are directed to new fully human fusion partner cell lines called human Karyochi cells, and to methods for making them. Human Karyochi cells are then fused with human antibody-secreting lymphoid cells to make fully human hybridomas called Karyochi-based hybridomas, which likewise secrete fully human monoclonal antibodies. Human Karyochi cells are made by isolating a donor nucleus that is substantially free of cytoplasm from either a first malignant B-lymphocyte cell line or a normal B-lymphocyte, and transferring the donor nucleus into the cytoplasm of a recipient cell from a second T- or B-lymphoid cell line. With time the nuclei synchronize and fuse to form the chimeric Karyochi fusion partner cell line. Nuclear transfer can be accomplished using intra-cytosolic nucleus injection or by impact-induced nucleus administration.

21 Claims, 2 Drawing Sheets

INTRA-CYTOSOLIC NUCLEUS INJECECTION

Human Myeloma Cell
FP1.0
(RECIPIENT CELL)

Human Lymphoblastoma
FP0-Agr-neo+

Retrieval of Nucleus
(DONOR NUCLEUS)

NUCLEUS TRANSFER

KARYotypic CHImaera or heteromyeloma
("KARYOCHI CELL")

Selection on HAT and G418

Human Hybridoma Fusion Partner Cell Line (Karyochi Cells)

FULLY HUMAN HYBRIDOMA FUSION PARTNER CELL LINES

CROSS-REFERENCE TO RELATED APPLICATIONS

This application claims benefit of Provisional Application No. 60/711,819, filed Aug. 26, 2005, the entire contents of which are hereby incorporated by reference as if fully set forth herein, under 35 U.S.C. §119(e)

STATEMENT OF GOVERNMENTAL INTEREST

This invention was made with Government support under Grant No. OC010016 awarded by the U.S. Army Department of Defense Program Project. The Government has certain rights in the invention.

FIELD OF THE INVENTION

This invention is in the field of fusion partner cell lines for use in making hybridomas that secrete fully human monoclonal antibodies.

BACKGROUND OF THE INVENTION

The seminal discovery by Kohler and Milstein (Kohler G, and Milstein C., Nature 1975; 256:495) of mouse hybridomas capable of secreting specific monoclonal antibodies (MAbs) against predefined antigens ushered in a new era in experimental immunology. Many problems associated with antisera were circumvented. Clonal selection and immortality of hybridoma cell lines assured monoclonality and permanent availability of antibody products. At the clinical level, however, the use of such antibodies is clearly limited by the fact that they are foreign proteins and act as antigens to humans.

Since the report of Kohler and Milstein, the production of mouse monoclonal antibodies has become routine. However, the application of xenogenic MAbs for in vivo diagnostics and therapy is often associated with undesirable effects such as a human anti-mouse immunoglobulin response. Progress in making fully human monoclonal antibodies has been hampered by the absence of human myelomas suitable for use as fusion partners with the desirable attributes of mouse myeloma cells such as stability, and high antibody production. The use of Epstein-Barr virus (EBV) has proved to be quite efficient for human lymphocyte immortalization (Kozbor D, and Roder J., J. Immunology 1981; 127:1275; Casual O, Science 1986; 234:476), but has certain limitations such as low antibody secretion rate, poor clonogenicity of antibody-secreting lines and chromosomal instability necessitating frequent subcloning.

Among the best potential fusion partners are syngenic myeloma cells with well-developed protein synthesis machinery. Nilsson K. and Ponten J., Int. J. Cancer 1975; 15:321. However, culturing difficulties explain why few lines have been conditioned for in vitro growth and capability to produce viable hybrids. Goldman-Leikin R E, J. Lab. Clin. Med. 1989: 113:335. Existing syngenic myelomas have low fusion yield and slow hybrid growth, although MAb production is relatively stable. Brodin T, J. Immunol. Meth. 1983; 60:1. Genetic instability, such as that which occurs when a mouse myeloma is used as the immortalizing partner with a human cell, is a major disadvantage of interspecies hybrids. Production of mouse-human cell hybrids is not difficult. In vitro these cells have growth characteristics similar to those of conventional mouse-mouse hybridomas. Teng N N H, Proc. Natl. Acad. Sci. (USA) 1983; 80:7308. However, spontaneous elimination of human chromosomes considerably reduces the probability of stable MAb secretion. Weiss M C, and Green H. Proc. Natl. Acad. Sci. (USA) 1967; 58:1104. In order to improve growth characteristics and stability of Hu-MAb production, heterohybrids between mouse myeloma cells and human lymphocyte (Oestberg L, and Pursch E., Hybridoma 1983; 2:361) as well as heteromyelomas (Kozbor D, et. al., J. Immunology 1984; 133:3001) have been used as the fusion partners. However, the problem remains that hybridomas made using murine/human heteromyelomas do not produce fully human antibodies.

Only one fully human fusion partner cell line has been reported. Abraham Karpas, et al. developed a fusion partner cell line (designated Karpas 707) from a patient who had multiple myeloma; it was not the product of cell fusion. Abraham Karpas, et al., PNAS Feb. 13, 2001, Vol. 98, No. 4, 1799-1804, and Vaisbourd, M., et al., Hybridoma and Hybridomics, Vol. 20, No. 5, 2001, 287-292, the entire contents of which are hereby incorporated by reference as if fully set forth herein. An ideal fusion partner cell line would not secrete any immunoglobulin and would have a short doubling time. Unfortunately Karpas 707 secretes gamma light chain and has a very slow doubling time of about 35 hours.

One attempt to overcome these problems has been to modify mouse monoclonal antibodies by linking rodent variable regions and human constant regions to make chimeric antibodies, or by grafting the complementarity-determining region gene segments from mouse antibodies into human genes to make humanized antibodies. These modifications reduce but do not eliminate the immunogenicity of the antibody. Phage display technology was developed for the in vitro generation of human monoclonal antibodies, and transgenic mice strains that contain human instead of mouse Ig genes have been developed. Bruggemann, M., et al. (1996) Immunol. Today 17, 391-97. These mice strains have human genes and make human antibodies, but the diversity in the strain is selected not in a human but in a mouse host, and the antibodies undergo affinity maturation in the mouse not a human environment. Immortalization of beta-lymphocytes with Epstein Barr Virus has also been tried, but the derived cells are typically unstable and secrete very small amounts of antibodies.

Thus there is a great need for fully human, natural fusion partner cell lines that do not produce any immunoglobulin, are stable, fuse well with human lymphocytes, and result in hybridomas that stably produce fully humanized antibodies.

SUMMARY OF THE INVENTION

Certain aspects of the present invention are directed to methods to make new fully human fusion partner cell lines called Karyochi cells that can be fused with antibody-secreting cells to make fully human hybridomas called Karyochi-based hybridomas, that likewise secrete fully human monoclonal antibodies. Some aspects are directed to the fully human antibodies made by the Karyochi-based hybridomas. Other aspects are directed to certain parent cells that can be used to make the Karyochi cells, including the human lymphoma cell line FP0 having Patent Deposit Designation Number PTA-7466, and the human myeloma cell line FP1.0 having Patent Deposit Designation Number PTA-7465. Certain aspects are further directed to the human chimeric fusion partner cell lines Karyochi-XX, which has Patent Deposit Designation Number PTA-7468, and Karyochi-7, which has Patent Deposit Designation Number PTA-7467.

An aspect of the invention is directed to Karyochi fusion partner cell lines (chimeric cells having nuclei from two different cells) and to methods for making them using cells from a single animal species, preferably from humans. Karyochi cells are made by isolating a donor nucleus that is substantially free of cytoplasm from either a first malignant B-lymphocyte cell line or a normal B-lymphocyte in the single animal species, transferring the donor nucleus into the cytoplasm of a recipient cell from a second T- or B-lymphoid cell line in the single animal species, and allowing time for the synchronization and fusion of the two nuclei in the recipient cell to form the chimeric Karyochi fusion partner cell line. Nuclear transfer can be accomplished using intra-cytosolic nucleus injection or by impact-induced nucleus administration. In some aspects of the invention the first and second human lymphoid cell lines are different human cell lines selected from the group including myeloma, lymphoma, multiple myeloma, lymphoblastoma and leukemia cell lines. While the preferred aspects of the invention involve making and using fully human Karyochi cells and Karyochi-based hybridomas to obtain fully human monoclonal antibodies, Karyochi cells and Karyochi-based hybridomas can be made using cells of any species of animal that makes antibodies, including all mammals, birds and reptiles.

Some embodiments of the invention are directed to Karyochi-based hybridoma that produce and secrete monoclonal antibodies, and to methods of making them. In a preferred embodiment the Karyochi-based hybridomas are fully human and make fully human monoclonal antibodies; however, Karyochi-based hybridomas can be made for any animal species. Human Karyochi-based hybridomas, for example, are made by obtaining a human Karyochi fusion partner cell that is made as described above, fusing it with a human antibody-producing lymphoid cell, and allowing time for the nucleus of the Karyochi cell and the nucleus of the lymphoid cell to synchronize and fuse to form the Karyochi-based hybridoma. The human antibody-producing lymphoid cell can be a splenocyte, a lymph node cell, a cell from Peyer's Patches, a peripheral blood lymphocyte, a B cell, a T cell, or a tonsil gland lymphocyte. In an aspect of the invention, the Karyochi-based hybridoma is made using lymphoid cell lines that each express a different selection marker including 8-Azaguanine resistance, 5-Bromouracil, 5-Fluorouracil or G-418 resistance. In some aspects of the invention the human antibody-producing lymphoid cell used to make a Karyochi-based hybridoma comes from a human having a condition causing the expression of an antigen associated with the condition, for example the condition is a disease such as bacterial infection and the antigen is a bacterial endotoxin, or the condition is cancer and the antigen is a cancer antigen. The Karyochi-based hybridoma will then be selected that produces human monoclonal antibodies that are specific or have high affinity for the antigen that is associated with the condition. In an aspect of the invention the lymphoid cells used to make the hybridomas come from an animal, preferably a human, that has a condition including diseases such as cancer, an infectious disease, an autoimmune disease, a disease associated with overepression of hormones or enzymes, graft vs. host disease, and cardiovascular disease. In certain embodiments the fully human monoclonal antibodies are specific or have high affinity for the antigen that can be a tumor-associated antigen, a cell specific antigen, a tissue-specific antigen, a hormone, an enzyme, a nucleic acid, a toxin, a viral antigen, a bacterial antigen, a fungal antigen, a parasitic antigen, a pyron, an enzyme, or a eukaryotic antigen.

BRIEF DESCRIPTION OF THE DRAWING

The present invention is illustrated by way of example, and not by way of limitation, in the figures of the accompanying drawings and in which:

FIG. 1. is a cartoon illustrating the method for constructing a Kayrochi Cell.

DEFINITIONS

Figure 1A:
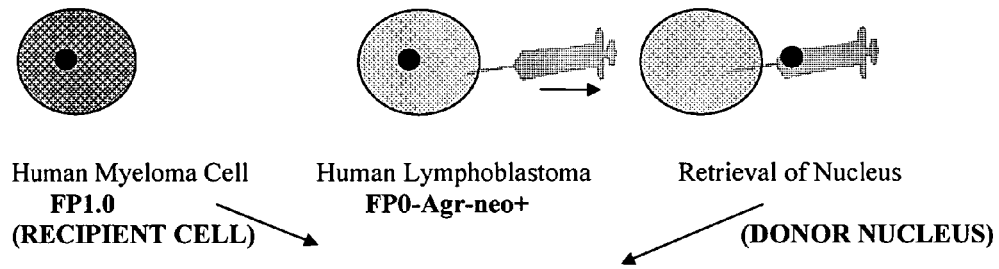
FIG. 1A illustrates the intra-cytosolic nucleus injection technique (ICN)

Unless otherwise defined, scientific and technical terms used in connection with the present invention shall have the broadest meanings that are commonly understood by those of ordinary skill in the art. Further, unless otherwise required by context, singular terms shall include pluralities and plural terms shall include the singular.

Generally, nomenclatures utilized in connection with, and techniques of, cell and tissue culture, molecular biology, and protein and oligo- or polynucleotide chemistry and hybridization described herein are those well known and commonly used in the art, as described in various general and more specific references such as those that are cited and discussed throughout the present specification. See e.g. Singleton et al., Dictionary of Microbiology and Molecular Biology 2.sup.nd ed., J. Wiley & Sons (New York, N.Y. 1994); Sambrook et al. Molecular Cloning: A Laboratory Manual (2d ed., Cold Spring Harbor Laboratory Press, Cold Spring Harbor, N.Y. (1989)), which are incorporated herein by reference.

Herein, "mammal" means any mammal, preferably a human.

The term "mammals other than humans" and "non-human mammals" used herein, are synomic to each other, meaning all mammals other than humans defined above.

The term "monoclonal antibody" as used herein refers to an antibody obtained from a population of substantially homogeneous antibodies, i.e., the individual antibodies comprising the population are identical except for possible naturally occurring mutations that may be present in minor amounts, and the term includes any fragment or portion thereof. Monoclonal antibodies are highly specific, being directed against a single antigenic site or epitope. Furthermore, in contrast to polyclonal antibody preparations which include different antibodies directed against different determinants (epitopes), each monoclonal antibody is directed against a single determinant on the antigen. As used herein, monoclonal antibodies are produced and secreted by Karyochi-based hybridomas. A fully human monoclonal antibody of this invention made by a fully human Karyochi-based hybridoma may be any human monoclonal antibody or a portion thereof having any isotype belonging to any class and any subclass of immunoglobulin including: IgG (IgG1, IgG2, IgG3, and IgG4), IgM, IgA (IgA1 and IgA2), IgD, IGD, and IgE or IgM. Examples of particularly preferable immunoglobulin of the present invention are those belonging to human-derived IgG (IgM, IgG1, IgG2, IgG3, or IgG4).

The term "epitope" is used to refer to binding sites for antibodies on protein antigens. Epitopic determinants usually consist of chemically active surface groupings of molecules such as amino acids or sugar side chains and usually have specific three-dimensional structural characteristics, as well as specific charge characteristics.

An "isolated" monoclonal antibody within the scope of the present invention is one that has been identified and separated and/or recovered from a component of its natural environment.

A "neutralizing monoclonal antibody" as used herein is a monoclonal antibody molecule that is able to eliminate or significantly reduce an effector function of a target antigen, such as a cancer antigen or tumor antigen, to which it binds. In an embodiment, a neutralizing antibody will reduce an effector function by 1-10, 10-20, 20-30, 30-50, 50-70, 70-80, 80-90, 90-95, 95-99, 99-100%.

Karyotype means the complete set of chromosomes of a cell or organism.

Karyogamy means the fusion of two or more nuclei.

Human Lymphoid cell line ("HuLCL") includes myeloma, multiple myeloma, lymphoma, lymphoblastoma, and leukemia cell lines.

Heteromyeloma means a cell line that combines genetic material from two different lymphoid cell lines by fusing whole cells from each lymphoid cell line; the term includes heterolymphomas. By contrast Karyochi cells are not formed from the fusion of two whole cells and therefore the resulting cells cannot be defined as heterohybridomas or heteromyelomas.

Hybridoma means an immortal antibody-producing cell line that stably produces antibodies, made by fusing cells from an immortal cell line (transformed) with an antibody-producing cell such as a beta lymphocyte.

Human-murine hybridoma means an immortal, antibody-producing cell line which results from the fusion of a murine heteromyeloma cell line with a human beta lymphocyte.

Donor Nucleus means an isolated nucleus from a lymphoid cell or lymphoid cell line (preferably human) which nucleus is substantially free of cytoplasm.

Recipient cell means a whole cell from a lymphoid cell line (preferably human).

Chimeric cell means a cell with chromosomes from two different heterogeneous cells.

Karyochi cell means a chimeric cell for use as a fusion partner cell line that is made using cells from a single animal species, preferably a human. To make a Karyochi cell, an isolated donor nucleus that is substantially free of cytoplasm is obtained from a normal B-cell or a B-cell line, and is then transferred into a whole recipient cell taken from a T- or B-lymphoid cell line. With time, the donor nucleus and the nucleus of the recipient cell fuse into a single nucleus thus making the chimeric Karyochi fusion partner cell. Karyochi cells are preferably made from donor nuclei and recipient cells that come from the same species, preferably human, however any species of animal that makes antibodies can be used including mammals, birds and reptiles. If the donor nucleus and the recipient cell are both taken from malignant B-cell lines, then they must be from different (heterogeneous) cell lines. Human Karyochi cells can be used to make fully human antibody-secreting hybridomas called Karyochi-based hybridomas. Various cell combinations can be used to make Karyochi Cells:

| RECIPIENT CELL | DONOR NUCLEUS | KARYOCHI CELL-TYPE |
|---|---|---|
| Malignant T-cell | Malignant B-cell | T/B chimeric cell |
| Malignant T-cell | Normal B-cell | T/B chimeric cell |
| Malignant B-cell, type 1 | Malignant B-cell, type II | B/B chimeric cell |
| Malignant B-cell | Normal B-cell | B/B chimeric cell |

Trioma means a cell that has three nuclei.

Antibody-producing lymphoid cell means any lymphoid cell from any species of animal that is capable of producing antibodies, such as a peripheral blood lymphocyte, a splenocyte, a lymph node cell, a B cell, a tonsil gland lymphocyte, or a Peyer's patch cell, preferably a human lymphoid cell.

Karyochi-based hybridoma means a monoclonal antibody-producing cell line, which results from the fusion of a Karyochi cell with an antibody-producing lymphoid cell. Preferably the Karyochi cell and the antibody-producing lymphoid cell come from the same species, preferably from a human, such that the Karyochi-based hybridoma produces and secretes fully human monoclonal antibodies. Karyochi-based hybridomas can be made using cells from any animal that makes antibodies including mammals, reptiles and birds.

T-cell (or T lymphocyte) means any of the lymphocytes that mature in the thymus and have the ability to recognize specific peptide antigens through the receptors on their cell surface.

B-cell means a type of lymphocyte that is capable of producing antibodies in response to detecting the presence of a particular antigen.

Specific monoclonal antibody means a type of antibody which binds specifically to a particular and certain antigen, epitope, cell or tissue, and does not bind to other antigens, epitopes, cells or tissues that are not particular and certain for the given antibody. High affinity monoclonal antibodies means antibodies which bind strongly to particular and certain antigens, epitopes, cells and tissues with an affinity constant ($K_a$) in the range $10^{-7}$-$10^{-13}$ M.

DETAILED DESCRIPTION OF THE INVENTION

Certain embodiments of the present invention are directed to new chimeric fusion partner cell lines named "Karyochi cells," which are defined herein, and to methods for making and using them. Karyochi cells are made by obtaining an isolated donor nucleus that is substantially free of cytoplasm; and transferring the isolated nucleus into the cytoplasm of a whole recipient cell. In a preferred embodiment the donor nucleus and the recipient cell come from the same animal species, preferably from a human. Where human cells are used, the donor nucleus comes from a lymphoid cell line, thus making either T/B or B/B chimeric Karyochi cells. The use of T-cells in constructing chimeric cells can be beneficial because T-cells secrete an array of autocrine and paracrine growth factors and cytokines that stimulate cell growth and antibody secretion. The CHImeric cell thus formed has two different KARYOtypes; hence the name "Karyochi cells." Because Karyochi cells are not formed from the fusion of two whole cells; the resulting cells cannot be defined as hetero-hybridomas or heteromyelomas. Karyochi cells are chimeric cells carrying two different sets of chromosomes derived from different cell types that preferably come from the same species. With time, the nuclei in the Karyochi cells synchronize and fuse to form a single nucleus. Human Karyochi cells are ideal fusion partner cell lines for forming fully human monoclonal antibody-producing hybridomas called "Karyochi-based hybridomas," which are defined herein. Karyochi cells can come from any animal that has antibody-producing cells, including all mammals, birds and reptiles.

The invention is further directed to methods for making Karyochi cells. The method includes: obtaining an isolated donor nucleus that is substantially free of cytoplasm from either a normal or malignant B-cell, for example using the techniques for nucleus isolation pioneered in in vitro fertilization. The preferred method for transferring the donor nucleus is intra-cytosolic nucleus injection of the donor nucleus into the cytoplasm of the recipient cell. Nuclear transfer can also be made by using impact-induced nucleus administration (IINI).

Certain embodiments of the invention are directed to Karyochi-based hybridomas, preferably fully human hybridomas capable of producing fully human monoclonal antibodies, and to methods for making them. In an embodiment, Karyochi-based hybridomas are obtained by fusing the described Karyochi cell (preferably human) with an antibody-producing lymphoid cell (preferably human), and selecting monoclonal antibody-producing Karyochi-based hybridomas that produce antibodies against an antigen of interest. The invention is further directed to the fully human monoclonal antibodies (hereafter "HuMAbs") made by human Karyochi-based hybridomas, and to any monoclonal antibodies made by Karyochi-based hybridomas in any species. Certain embodiments are also directed to monoclonal antibodies that are made from cells that all derive from the same species, thus making the antibodies fully compatible with that species. According to an embodiment of this invention, hybridoma replication is effective both in vitro or in vivo. Karyochi-based hybridoma cells can therefore grow in Petri dishes, flasks, wells or bioreactors as well as in vivo in immunocompromised mice, for example. In certain embodiments the human antibody-producing lymphoid cell is taken from a patient having a condition, such as a disease including an infection or cancer, which condition results in expression of at least one antigen associated with the presence of the condition in the animal (for example a disease-specific, condition-specific or tumor-associated antigens). In certain embodiments human Karyochi-based hybridomas are made using antibody-secreting cells from a subject known to be infected or diseased or having the condition of interest. Isolated fully HuMAbs made by these hybridomas are then screened for specificity or affinity for an antigen known to be associated with the infection, disease or condition. Such HuMAbs can then be used therapeutically or diagnostically using methods known in the art. In certain embodiments the isolated fully human (or other species) monoclonal antibodies are bound to a toxin or a radionuclide that can kill the target cells expressing the antigen. All of the examples herein are for making fully human Karyochi cells, Karyochi-based hybridomas and monoclonal antibodies.

A good fusion partner cell line for making fully human monoclonal antibody-producing hybridomas should ideally meet the following requirements. It should:
 be fully human in origin;
 produce no or negligible amounts of endogenous immunoglobulin or individual immunoglobulin chains;
 have a short doubling time;
 grow in suspension culture;
 be suitable for high efficiency fusion with B-cells of different histological origin;
 be non-biased (non-selective in terms of Ig type) in fusion to B-cells producing different Ig isotypes;
 yield stable Ig-producing hybrids capable of long-term stable production of specific Ig's; and
 be easily adaptable to serum- and protein-free media and culturing in bioreactors for mass production of monoclonal antibodies.

Until now there was no fully human fusion partner cell line that met these criteria.

In our earlier work we developed the heteromyeloma fusion partner cell line called MFP2 (ATCC Designation Number HB-12482), which is one of the better fusion partner cell lines presently available. MFP2 cells have been studied thoroughly and are the subject of U.S. Pat. No. 6,197,582, the entire contents of which are hereby incorporated by reference as if fully set forth herein. Yet as good as MFP2 cells are, they are not fully human as they are formed from fusing mouse myeloma 653 cells and human myeloma RPMI 8226 cells. Table 1 compares the general characteristics of several fusion partner cell lines (MFP2, X63, 653, RPMI-8226, and B6B11) of animal and human origin. As Table 1 shows, RPMI-8226 by itself is not a good fusion partner cell line. It produces IgG light chain, has insignificant levels of fusibility with other cells, and very low fusion efficiency. However RPMI fused with mouse Myeloma 653 made the MFP2 cell line, which is a good fusion partner cell line (FPCL) despite the fact that it is not fully human.

Abraham Karpas, et al. have reported the only potentially useful fully human fusion partner cell line, which is designated Karpas 707. Abraham Karpas, et al., PNAS Feb. 13, 2001, Vol. 98, No. 4, 1799-1804, and Vaisbourd, M., et al., Hybridoma and Hybridomics, Vol 20, No. 5, 2001, 287-292, the entire contents of which are hereby incorporated by reference as if fully set forth herein. Karpas 707 was established from a patient who had multiple myeloma, however, it was not the product of cell fusion. Karpas 707 cells secrete gamma light chain and have a very slow doubling time of about 35 hours. A report analyzing the variable regions of antibody heavy and light chains from the Karpas 707 heterohybridomas showed that they were representative of human B lymphocytes with respect to family use, segment use, somatic mutation and chain pairings. The combination of long doubling time and the production of IgG light chain by Karpas 707 make it less than ideal as a human fusion partner cell line. Fusion efficiencies for Karpas 707 cells have not been reported.

Karyochi Cells: Formation and Characteristics

Certain embodiments of the present invention are directed to new human fusion partner cell lines (FPCL) called Karyochi cells for making fully human, antibody-producing hybridomas called Karyochi-based hybridomas. Karyochi cells meet all of the criteria listed above for an ideal human fusion partner cell line. Unlike the known hybrid fusion partner cells that are made using cells from two different species and from the fusion of two whole cells, Karyochi cells are made using cells from the same species and they are not formed from the fusion of two whole cells. Instead, Karyochi cells are made by transferring an isolated donor nucleus that is substantially free of cytoplasm taken, for example from a normal or a malignant B cell, into the cytoplasm of a whole recipient cell taken from a different lymphoid cell line. The chimeric cell thus formed has two different karyotypes; hence the name "Karyochi cells" to distinguish them from cells made by the fusion of two whole cells. In the preferred embodiment Karyochi cells are fully human. After nuclear transfer, the two nuclei in the Karyochi cell eventually synchronize and fuse. Karyochi cells are aneuploid, i.e. human Karyochi cells don't have a typical 23 homologous pair set of human chromosomes. In those Karyochi cells where both the donor and recipient cells come from transformed cells, significant chromosome instability is usual. Human Karyochi cells typically have more than 46 chromosomes. When two karyotypes are combined they don't form a stable karyotypic chimera in which the number of chromosomes is a simple arithmetic sum. The cells undergo chromosome elimination over time after chimerization until the karyotype is stabilized. The karyotype for chimeras of transformed cells usually is presented as a mode, i.e. a range of chromosome number which can be found in individual cells from the same cell line. Preliminary studies estimate that human Karyochi cells have a modal number of between about 120 to about 140 chromosomes.

The decision to use heterogeneous cell types for the donor and recipient cell nuclei was based on previous experience in traditional whole cell fusion which showed that heterohybridomas and heteromyelomas perform much better in fusing with human lymphocytes to make hybridomas than either parental cell lines separately. Ostberg L. Human monoclonal antibodies in transplantation, Transplant Proc. 1992 August; 24(4 Suppl 2):26-30; Ostberg L, Pursch E. Human X (mouse X human) hybridomas stably producing human antibodies, Hybridoma. 1983; 2(4):361-7; Nilsson K, et al., Entrapment of animal cells for production of monoclonal antibodies and other biomolecules, Nature. 1983 Apr. 14; 302(5909):629-30; Ostberg L. Human X (mouse X human) hybridomas, Methods Enzymol. 1986; 121:228-34; Isaacson C. et al., Human and primate monoclonal antibodies for in vivo therapy, Clin Chem. 1988 September; 34(9):1681-8, the entire contents of which are hereby incorporated by reference as if fully set forth herein. Lymphoid cell lines suitable for making Karyochi cells include myeloma, lymphoma, lymphoblastoma and leukemia. In an embodiment, Karyochi cells are formed by fusing a donor cell from a T- or B-lymphoid cell that is not transformed with a cell from a lymphoid cell line.

In a preferred embodiment, the donor nucleus is isolated using the Intra-Cytosolic Nucleus Injection (ICNI) technique that is used to isolate nuclei from a sperm for in vitro fertilization (IVF). Trokoudes K M, et al., Pregnancy with spermatozoa from a globozoospermic man after intracytoplasmic sperm injection treatment Hum Reprod, 1995 April; 10(4): 880-2; Hlinka D, et al., A modified method of intracytoplasmic sperm injection without the use of polyvinylpyrrolidone, Hum Reprod. 1998 July; 13(7):1922-7; Katayose H, et al., Efficient injection of bull spermatozoa into oocytes using a Piezo-driven pipette Theriogenology, 1999 November; 52(7):1215-24, the entire contents of which are hereby incorporated by reference as if fully set forth herein. This method involves removing the nucleus from the donor cell so that it is substantially free of cytoplasm using an ultra thin micromanipulator needle (diameter<5 um) and injecting the nucleus into the cytoplasm of the whole recipient cell. The recipient cell typically has a diameter of about 30-60 micrometers and a volume at average of about 50,000 micrometers$^3$. The volume of the donor nucleus (largely free of cytoplasm) varies substantially but is typically about 150 micrometers$^3$, which is about 0.3% of the recipient cell volume. Thus, the new methods of the present invention that use a donor nucleus substantially free of cytoplasm (rather than a whole donor cell) to form fusion partner cell lines cause negligible disruption to the infrastructure of the cytoplasm and negligible alteration of the volume of the recipient cell. Moreover, disruption of the cytoplasm of the recipient cell is limited to the site of insertion of the donor nucleus. Endoplasmic reticulum and Golgi apparatus throughout the recipient cell remain essentially intact. It is speculated that the minimum disruption of the recipient cell in making Karyochi cells accounts at least in part for their improved success for making stable monoclonal antibody-producing Karyochi-based hybridomas.

Methods for ICNI and other methods of nucleus transfer are described more fully in: Khalili M A, et al., J Assist Reprod. Genet. 2002; 19: 84-6; and in K. D. Nusser, et al., Human Reproduction, Vol. 16, No. 1, 130-137, the entire contents of which are hereby incorporated by reference as if fully set forth herein. Regarding methods for the isolation and purification of nuclei, we reference Deborah L. Hodge, et al., Molecular and Cellular Biology, 2002, p. 1742-1753, Vol. 22, No. 6; and Dijkwel, P. A., et al., *Mol. Cell Biol.* 1991, 11, 3850-3859, the entire contents of which are hereby incorporated by reference as if fully set forth herein.

Figure 1B:
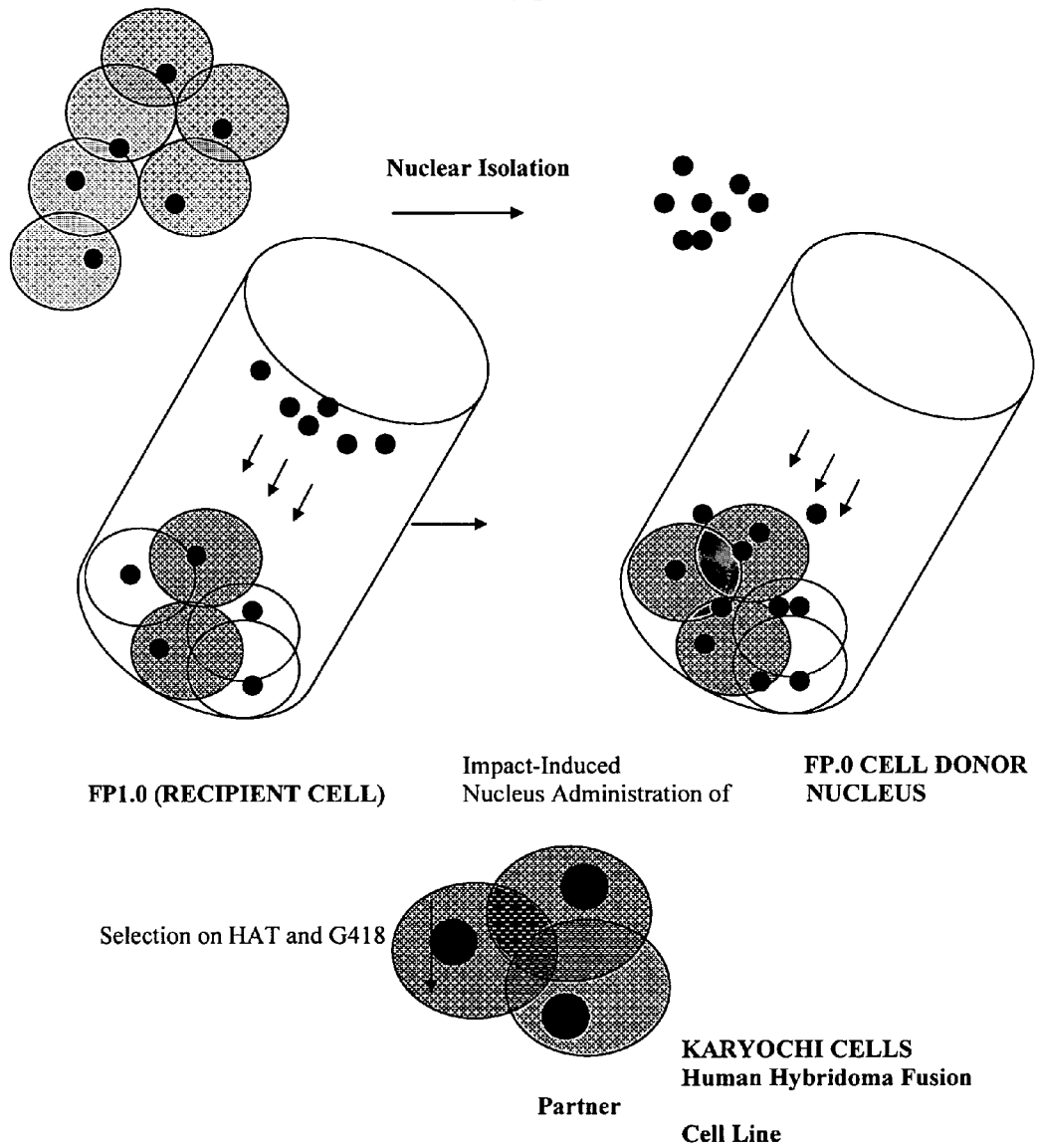
FIG. 1B illustrates the impact-induced nucleus administration method (IINA).

In another embodiment, the donor nucleus is forced into the recipient cell cytoplasm using Impact-induced Nucleus Administration (IINA). Wallace D C, et al., J Cell Biol. Cytoplasmic transfer of chloramphenicol resistance in human tissue culture cells. 1975 October; 67(1):174-88; Jeon, K. W. J Selective effects of enucleation and transfer of heterologous nuclei on cytoplasmic organelles in Amoeba proteus Protozool, 1975 August; 22(3):402-5; Appels R, et al., The first division of HeLa times chick erythrocyte heterokaryons. Transfer of chick nuclei to daughter cells, Exp Cell Res. 1975 April; 92(1):79-86, the entire contents of which are hereby incorporated by reference as if fully set forth herein. In the IINI method purified donor nuclei substantially free of cytoplasm are isolated by lysing cells and separating the nuclei in a sucrose gradient. After several washings the nuclei are pelleted, resuspended in 0.5% albumin and 10% sucrose/PBS, counted and prepared for IINA. The isolated nuclei are then pelleted onto a bed of recipient cells under the several hundreds of G-force using a centrifuge. When a force of between 400-500 g is applied, a certain fraction of the donor nuclei penetrate the recipient cell membrane and integrate with the cell cytoplasm without disrupting or damaging the recipient cell. FIG. 1 A is a cartoon of the method of making a Karyochi cell using ICNI; FIG. 1B is a cartoon of the method of making a Karyochi cell using IINA. Cells that receive more than one nucleus usually do not survive. The selection of a Karyochi cell is done by culturing the recipient cells in the presence of HAT and G418, two selective markers that allow for the survival of only chimeric cells while recipient cells that did not receive a donor nucleus will die.

Various combinations of cells can be used to make Karyochi cells. Some combinations are shown in Table 2.

TABLE 1

GENERAL CHARACTERISTICS OF FUSION PARTNER CELL LINES

|  | Karyochi-7 | MFP-2 |
| --- | --- | --- |
| Origin | human heteromyeloma | trioma {(mouse × human) heteromyeloma × human lymphocyte} |
| Karyotype (modality) | 120-140 | 80-90 |
| Doubling Time (hours) | 20 | 20-22 |
| Product (Ig) | none | none |
| Fusibility | human PMNC, Lymph Node | human, monkey LN, PBL, tonsils, spleen |
| Fusion Efficiency | >1 per $10^5$ | 1 per $10^5$ |
| Fusion Efficiency PEG | high (>1 per $10^5$) | high |
| Fusion Efficiency ELEC | high (>1 per $10^4$) | high |

TABLE 1-continued

GENERAL CHARACTERISTICS OF FUSION PARTNER CELL LINES

| | | Karyochi-7 | MFP-2 |
|---|---|---|---|
| Hybridoma | Ig-Products | IgG, IgM | IgM, IgG, IgA, IgE(D)? |
| | Ig-Levels | up to 30 ug/ml/24 hrs/$10^6$ cells | up to 400 ug/ml/24 rs/$10^6$ cells (one instance) |
| Glycosylation | | likely human (galactose rich) | likely human (galactose rich) |
| Clonogenicity | | high | high |
| Stability (hybridomas) | | 9-10 months | more than 5 years |
| Serum-free medium | | yes | yes |
| Ascites Production | | yes, in immunodeficient mice | no |
| Bioreactor Production | | yes | yes |
| Resistance to alloreactivity | | yes (G418$^{res}$) | yes for a MFP-2-S clone |
| Transfectable | | ND | yes (at least one example) |

ND = no data

TABLE 2

Cell Combinations for Making Karyochi Cells

| RECIPIENT CELL | DONOR NUCLEUS | KARYOCHI CELL TPE |
|---|---|---|
| Malignant T-cell | Malignant B-cell | T/B chimeric cell |
| Malignant T-cell | Normal B-cell | T/B chimeric cell |
| Malignant B-cell, type 1 | Malignant B-cell, type II | B/B chimeric cell |
| Malignant B-cell | Normal B-cell | B/B chimeric cell |

Twelve fully human Karyochi fusion partner cell lines have been made thus far. They are named Karyochi 1-6, Karyochi XX, and descendants of Karyochi XX named XX1, XX-3, XX-5, XX-7 and XX-10. The lineage of Karyochi cell lines 1-6 and XX are set forth in Table 3. Karyochi-XX was a population of karyotypic hybrid cells generated using FP0 lymphoblastoma as the donor nucleus and FP1.0 myeloma as the recipient cell. This population (Karyochi-XX) was then cloned using a single cell cloning procedure that is well known in the art and widely used in hybridoma development. 10 subclones labeled Karyochi-XX-1 through Karyochi-XX-10 were selected for further evaluation of their fusion efficiency and ability to form stable hybridomas. One of these subclones, Karyochi-XX-7 (hereafter "Karyochi-7") manifested superior properties and was chosen for further work. Karyochi-7 is a stable cloned karyotypic hybrid fusion partner cell line derived from parent cells FP0 and FP1.0. Certain embodiments are directed to Karyochi-7 cells, which have been deposited with the American Type Culture Collection, located at 10801 University Blvd., Manassas, Va. 20110-2209, USA (ATCC) and have Patent Designation Number PTA-7467; and to Karyochi-XX cells that have also been deposited with the ATCC with Patent Designation Number PTA-7468. Cell lines Karyochi-7 (PTA-7467), Karyochi-XX (PTA-7468), FP1.0 (PTA-7465) and FP0 (PTA-7466) were deposited with the ATCC on Apr. 4, 2006.

TABLE 3

GENEALOGY OF KARYOCHI CELLS

| Karyochi cell line | Donor Nucleus Origin | Recipient Nucleus Origin |
|---|---|---|
| Karyochi-1 | Normal B-cell | FP0 lymphoblastoma cell |
| Karyochi-2 | Normal B-cell | RPMI 8226 lymphoblastoma cell |
| Karyochi-3 | FP1.0 myeloma cell | FP3 lymphoblastoma cell |
| Karyochi-4 | FP2 lymphoblastoma cell | FP3 lymphoblastoma cell |
| Karyochi-5 | FP3 lymphoblastoma cell | RPMI 8226 lymphoblastoma |
| Karyochi-6 | FP0 lymphoblastoma | FP2 myeloma cell |
| Karyochi-XX(clones from 1 to 10) | FP0 cells Hodgkin's lymphoma biopsy | FP1.0 cells myeloma biopsy |

Eight fully human Karyochi-based hybridoma cell lines secreting fully human monoclonal antibodies were made using Karyochi fusion partner cell lines 1, 2, 5, XX-1, XX-3, XX-5, Karyochi-7, and XX-10 fused with human lymphoid antibody-producing cells from PBL, spleen and lymph nodes. Tables 4 and 5 show various characteristics of these Karyochi-based hybridomas. Based on the data in Tables 4 and 5, the Karyochi-7 cell line (an FP.0×FP1.0 descendant of Karyochi XX) was chosen as the preferred fusion partner cell line for optimizing monoclonal antibody-producing hybridomas. It is expected that various Karyochi cell lines will be preferred depending on the human monoclonal antibody-producing lymphoid cell selected for hybridoma fusion.

TABLE 4

KARYOCHI-BASED HYBRIDOMAS

| Karyochi-based hybridoma series # | Fusion Partner Cell Line = Karyochi Cell | Human Lymphoid Cell | Fusion Efficiency (PEG, $10^{-5}$) | Stability Over Time (mo) | Production ug/ml/ 24 hrs/ $10^6$ cells (range) |
|---|---|---|---|---|---|
| Karyochi-based hybridoma #1 | Karyochi 1 | PBL, spleen, node | 0.1-0.3 | 1.5 | 0.5-1 |
| Karyochi-based hybridoma #2 | Karyochi 2 | PBL, spleen, node | <0.1 | 1 | 1-2 |
| Karyochi-based hybridoma #3 | Karyochi 5 | PBL, spleen, PBL froz | 0.3-0.4 | 2.5 | 0.5-1 |
| Karyochi-based hybridoma #4 | Karyochi XX.1 | PBL, spleen, PBL froz | 1-2 | 5 | 2-3 |

TABLE 4-continued

KARYOCHI-BASED HYBRIDOMAS

| Karyochi-based hybridoma series # | Fusion Partner Cell Line = Karyochi Cell | Human Lymphoid Cell | Fusion Efficiency (PEG, $10^{-5}$) | Stability Over Time (mo) | Production ug/ml/ 24 hrs/ $10^6$ cells (range) |
|---|---|---|---|---|---|
| Karyochi-based hybridoma #5 | Karyochi XX.3 | PBL, node | 1-2 | 5 | 0.5-1 |
| Karyochi-based hybridoma #6 | Karyochi XX.5 | PBL, spleen, node | 0.5-0.6 | 4 | 8-10 |
| Karyochi-based hybridoma #7 | Karyochi XX.7 [Karyochi 7] | PBL, spleen, node, PBN froz | 5-10 | 9-10 | 25-30 |
| Karyochi-based hybridoma #8 | Karyochi XX.10 | Spleen, node | 2-3 | 5-6 | 5-8 |

An example of making Karyochi cells is described with reference to the fully human Karyochi-XX cell line that was made with donor nuclei from human FP0 cells established in culture from a biopsy taken from a Hodgkin's lymphoma patient. Karyochi 7 fusion partner cells are a descendant of Karyochi XX. FP0 cells have a mixed phenotype indicating their T-cell origin: CD3+CD4+CD19−CD20−CD45−CD38−CD33−CD34−CD138−λ−κ−a; these cells have been deposited with the American Type Culture Collection (ATCC) and have Patent Deposit Designation number PTA-7466 to which an embodiment of the invention is directed. FP0 cells have an irregular shaped morphology, and they grow in clumps in suspension. FP0 cells were mutagenized by ultraviolet light, and those cells with a dual resistance to 8-Azaguanine (8-Ag) (designated "FP0-AgR cells") and sensitivity to HAT (Hypoxanthine, Aminopurine, and Thymidine) were selected. FP0 stands for Fusion Partner Zero. FP0-AgR cells were then transfected with Neo+ plasmid that confers Geneticin G418 resistance, and Geneticin G418-resistant clones were selected. The resulting cells designated "FP0-AgR-neo+ cells" were used as nuclei donors. Certain embodiments of the present invention are directed to the FP0-AgR-neo+ cell line, deposited with the ATCC.

TABLE 5

KARYOCHI FUSION PARTNER CELLS: GROUP CELL CHARACTERISTICS

| | Karyochi-XX.7, (Karyochi-7) | Karyochi-XX.10 | Karyochi-XX.3 | Karyochi-XX.1 |
|---|---|---|---|---|
| Doubling Time (hr) | 20-22 | 24-26 | 30-32 | 20-22 |
| Product (endogenous Ig) | None | None | None | Traces of lambda chain |
| Fusibility | SPL, LNL, PBL | LNL, PBL | SPL, LNL | SPL, LNL |
| Fusion Efficiency | >1 per $10^5$ | 2-3 per $10^5$ | 1-2 per $10^5$ | 1-2 per $10^5$ |
| Hybridoma Ig Products | IgG, IgM, IgA | IgG, IgM, IgA | IgG, IgM | IgM |
| Hybridoma Ig Levels ug/ml/24 h/$10^6$ cells | 25-30, one instance of up to 300 | 5-8 | 1-2 | 1-2 |
| Clonogenicity | high | medium | medium | medium |
| Stability (hybridoma), mo | 9-10 | 5-6 | 5 | 5 |
| Serum-free medium | Yes | NT | NT | No |
| Ascites Production | Yes in immuno-deficient mice | NT | NT | NT |
| Bioreactor Production | Yes | YES | YES | NT |

The whole recipient cells used to make Karyochi XX and Karyochi-7 cells were human FP1.0 cells, which were established in culture from a biopsy taken from a myeloma patient. FP1.0 cells were not mutagenized and the original "wild" type was used as the recipient cell to the Karyochi cells. An embodiment is directed to FP1.0 cells that have been deposited with the ATCC and have been given Patent Deposit Designation Number PTA-7465; they have the following phenotype: $CD38^+CD56^+CD138^+CD45^-CD19^-CD20^-CD3^-CD4^-CD10^+CD33^-CD34^-\lambda^-\kappa^-$. FP1.0 wild type cells have a round shape appearance; and they grow in suspension reaching densities close to $2\times10^6$ cells/ml in standard RPMI-1640 media. To make the Karyochi cells, the isolated donor nucleus from the FP0-AgR-neo$^+$ cell was microinjected into the cytoplasm of the whole recipient FP1.0 cell. The injection series included 20-30 cells at approximately 3 cells in a microdrop.

Both the ICNI and IINA methods for transferring the isolated donor nucleus to the whole recipient cell result in a dikaryon (a cell carrying two nuclei); one is the recipient's original nucleus and another one is the donor nucleus. During metaphase of the first mitotic division following donor nucleus injection, the nuclei fuse and the chromosomes from both nuclei mix up. After the recipient cell divides, the resulting daughter cells carry the mixed karyotype consisting of chromosomes from both parental cells in a single nucleus. To select true Karyochi cells, recipient cells carrying the donor nucleus were incubated for 48 hours after which time they were put in media with the selective agents HAT and G418. Only true chimeras called Karyochi cells could live on this selective medium. The cells that did not receive the donor nucleus die in the presence of HAT. Similarly, cells that received the donor nucleus but for some reason lost their own nucleus die in the presence of G418. Only Karyochi cells having a donor nucleus (FP0-AgR-neo$^+$) and a nucleus from the recipient cell (FP1.0) can live in the presence of HAT and G418.

TABLE 6

KARYOCHI-7 -vs- KARPAS 707 COMPARISON

| | Karyochi-7 | Karpas 707 |
|---|---|---|
| Karyotype (Modal Number) | 120-140 | 210-220 |
| Doubling Time | 20 hours | 35 hours + |
| IgG Product | NONE | IgG light chain |
| Fusibility | PMNC, lymphocytes, lymph nodes, splenocytes, epithelial cells | human tonsils, Epstein-Barr transformed cells (164 cells) |
| Fusion Efficiency (general) | >1 per $10^5$ | No information |
| Fusion Efficiency PEG | high (>5 per $10^5$) | No information, apparently sensitive to PEG |
| Fusion Efficiency ELECTRO | high (>10 per $10^4$) | High |
| Hybridoma IgG Products | IgG, IgM, IgA | IgG, IgM |
| Hybridoma IgG levels | 25-30 ug with one instance of up to 300 ug/ml/24 hrs/$10^6$ cells | 21.0 ug/ml/ 24 hrs/$10^6$ cells |
| Clonogenicity | High | No information |
| Stability FPCLs | High, 10 months at least without cloning | No information |
| Stability Hybridomas | 9-10 months or more | 5 months or more |
| Serum-free Media | Yes | No information |
| Ascites | No, except in immunodeficient mice | No information |
| Bioreactor | Yes | No information |
| Glycosylation of MAbs | likely human, galactose rich no direct data | No information |
| Resistance to alloreactivity | Yes, G418 marker | No information |

As Tables 4 and 5 show, not all Karyochi cells have the same characteristics with respect to fusibility, fusion efficiency, clonogenicity, the ability to thrive in serum-free medium, and the ability to be produced in ascitic fluid or in a bioreactor. Table 6 shows that Karyochi-7 cells compare favorably to fully human Karpas 707 fusion partner cell lines. Karyochi-7 cells have a doubling time of about twenty (20) hours which is slightly better than the doubling time of 20-22 hours for MFP2 cells (Table 1). Moreover, Karyochi-7 cells reproduce substantially faster than Karpas-707 cells that have a thirty-five (35) hour doubling time. Like MFP2 cells, Karyochi-7 cells produce no immunoglobulin which is highly desirable in a fusion partner cell line. By contrast Karpas 707 cells produce light lambda chain IgG molecules. Karyochi-7 cells are capable of fusing with human polymorphonuclear cells (PMNC), lymph node cells, lymphocytes and splenocytes. Karpas 707 cells have been reported to form heterohybridomas with an Epstein-Barr virus-transformed cell line (164 cells), with fresh tonsil cells and white blood cells from peripheral blood to produce stable hybrids that did not loose immunoglobulin secretion over five months of continuous growth. The Karyochi-7 cell line has been stable over a period of 12 months maintaining its doubling time and fusion efficiency. Importantly, Karyochi-based hybridomas made using Karyochi-7 cells as the fusion partner cell line have been comparably stable over a period averaging 7 months; the longest hybridoma monitored was stable for 10 months, see Table 4. Karyochi cells, especially Karyochi-7 cells to which certain embodiments are directed, are ideal fusion partners. They are fully human in origin, produce no or negligible amounts of endogenous immunoglobulin or individual immunoglobulin chains, have a short doubling time, grow in suspension, have high efficiency fusion with B-cells of different histological origin, are non-biased (non-selective in terms of Ig type) in fusion to B-cells producing different Ig isotypes, yield stable Ig-producing hybrids capable of long term stable production of specific immunoglobulins, and are easily adaptable to serum-free media and culturing in bioreactors for mass production of monoclonal antibodies. Fusion Efficiency is very important in a fusion partner cell line. Karyochi-7 cells have good fusion efficiencies of >1 per $10^5$ lymphoid cells, which compares favorably to MFP2 cells, X63.653 mouse plasmacytoma cells (See Table 1), and B6B11 heteromyeloma cells (See Table 1). The fusion efficiency of Karyochi-7 cells in PEG is high (>1 per $10^5$), and it is even better using electrofusion (>1 per $10^4$). Zimmerman U., et al. Hum. Antibodies Hybridomas 1995; 6(2):77-80, the contents of which are hereby incorporated by reference.

Importantly, Karyochi-based hybridomas produce high levels of IgG and IgM (up to 300 ug/ml/24 hrs/$10^6$ cells), which is comparable to the levels produced by MFP2 hybridomas and Karpas 707 cells. Karyochi-based hybridomas are non-biased (non-selective in terms of Ig type) in fusion to B-cells producing different Ig isotypes. Karyochi-based hybridomas made with Karyochi-7 cells produce high levels of IgG, IgA and IgM (up to 300 ug/ml/24 hrs/$10^6$ cells), which is comparable to the levels produced by MFP2 hybridomas and Karpas 707 cells. Karyochi-based hybridomas made with Karyochi-7 cells are also adaptable to serum-free media and culturing in bioreactors for mass production of fully human monoclonal antibodies. Moreover, Karyochi-7 cells fuse very well with lymphocytes using PEG format of fusion, while the Karpas 707 cell line is sensitive to PEG.

Formation of Karyochi-Based Hybridomas

Certain embodiments of the present invention are directed to Karyochi-based hybridomas made by fusing a Karyochi cell, preferably human, with an antibody-producing lymphoid cell (preferably human), including a peripheral blood lymphocyte, a splenocyte, a lymph node cell, a B cell, a T cell, a tonsil gland lymphocyte, a monocyte, a macrophage, an erythroblastoid cell or a Peyer's patch cell. Karyochi-based hybridomas have been made using various Karyochi cells and human lymphoid cell combinations as indicated in Table 5.

One particular hybridoma series designated Karyochi-based hybridoma #7 (Table 4) was made by fusing Karyochi-7 cells with human spleen cells. Karyochi-based hybridoma #7 was cloned by limiting dilutions using Hybridoma Cloning Factor (Origen 50-0615) according to methods that are known in the art. Fazekas de St. Groth, S., et al. Journal of Immunological Methods 35: 1-21 (1980); Sugasawara, R., Journal of Tissue Culture Methods 12: 93-95, (1989); and Sugasawara, R., Bio/Technology 6: 895-902 (1988), the entire contents of which are hereby incorporated by reference as if fully set forth herein. The supernatants of the hybridomas were screened for the presence of nonspecific immunoglobulin secretion according to methods known in the art that are described in Example 1. Karyochi-based hybridoma #7 (not to be confused with Karyochi-7, a fusion partner cell line) made all classes of fully human monoclonal antibodies (IgG, IgM and IgA) at a level of up to about 300 ug/ml/24 hrs/$10^6$ cells (one instance), and has been stable for 9 months in culture. It continues to thrive, multiply, produce and secrete antibodies. In one embodiment the invention is directed to a method for making human monoclonal antibody-producing Karyochi-based hybridomas by obtaining a human Karyochi cell, fusing the Karyochi cell with a human lymphoid cell, allowing time for the nuclei from the Karyochi cell and the lymphoid cell to synchronize and fuse, incubating the fused cell under conditions permissive to the production of antibody, determining whether the fused cell produces monoclonal antibody, and if it does, selecting and identifying the cell as a Karyochi-based hybridoma.

In our earlier work we showed that lymph node-derived hybridomas from a thyroid cancer patient produced anti-thyroglobulin antibodies. Kalantarov G, Rudchenko S, Trakht I, Human Antibodies, 11, 3, 2002, pp. 85-96, the contents of which are hereby incorporated by reference. This was an unexpected result because the patient had no known history of autoimmune (i.e. anti-thyroid antibodies) disease. This showed that the antibodies produced in this patient to thyroglobulin were induced by the presence of cancerous thyroid adenocarcinoma cells, which are known to secrete thyroglobulin. Thus it was shown that tumor cells in a patient can induce a humoral immune response to tumor-associated antigens. It also showed that antibody-producing cells can be identified and immortalized by fusing lymphocytes from a patient having cancer with a fusion partner cell line in order to produce a hybridoma that secretes anti-tumor monoclonal antibodies.

Similar results were obtained and are described in U.S. Pat. No. 6,197,582 for human breast cancer, the entire contents of which are hereby incorporated by reference as if fully set forth herein. Axillary lymph nodes were excised from breast cancer patients who underwent mastectomy or lumpectomy. Lymphocytes isolated from these lymph nodes were fused to MFP-2 fusion partner cells. Monoclonal antibodies produced and secreted by the resulting hybridomas were then screened against breast cancer cell lines MCF7, SK-BR-3, ZR-75-1. Nearly all the hybridomas produced IgG or IgM (approximately 85% and 10% respectively). Nearly 15% of the hybridomas assayed against breast cancer cell lines produced antibodies specifically directed against breast cancer cells. The hybridoma supernatants were tested in two ways: (1) on live cells in the CELISA (cellular ELISA) assay and (2) by Western blotting using cell lysates. Even a patient who had received 77 cycles of chemotherapy which would reasonably be expected to have a depressing effect on the patient's immune system, none-the-less produced anti-cancer antibodies suitable for fusing with fusion partner cell lines to make hybridomas. Trakht I., et al. unpublished data. These methods are known in the art and can be used to test isolated fully HuMAbs made by Karyochi-based hybridomas.

Karyochi-based hybridomas can be similarly made using B-lymphocytes taken from an animal, preferably a human, having a disease or condition such as cancer or an infection. The molecular weight range of the specific antigens recognized by human monoclonal antibodies can be determined using known methods. In order to delineate the nature of the antigenic target, immunoprecipitation followed by microsequencing can be performed. In addition, random peptide combinatorial libraries can be used to identify the molecular targets of the cancer-specific antibodies. Birch-Machin I., et al. J. Virol. Methods. 2000; 88(1): 89-104, the contents of which are hereby incorporated by reference. Human monoclonal antibodies can also be screened against known cancer-specific antigens that have been described as potential targets for the immunotherapy of cancer, including HER2/neu, Mucin 1 and Mucin 2, p53, c-myc, blood antigens T, Tn and sialyl-Tn, tuncated form of EGF, Lewis-Y antigen and others. The presence of circulating antibodies to these antigens has been described in cancer patients. Moller G., 1995, the contents of which are hereby incorporated by reference. HuMAbs can be made against any cancer antigen, including lung cancer, liver cancer, leukemia, lymphoma, neuroblastoma, glioma, meningioma, bone cancer, thyroid cancer, breast cancer or prostate cancer.

Infectious diseases are commonly accompanied by a well-developed humoral and cellular immune response. Patients with certain infections often contain large numbers of specific antibody-producing lymphocytes that can be used to generate Karyochi-based hybridomas. Infected individuals also tend to over express the proinflammatory cytokines and lymphokines, including tumor necrosis factor alpha and interleukin-1a, which are involved for example in septic shock. These cytokines can be neutralized by the isolated human monoclonal antibodies from Karyochi-based hybridomas. Additional targets for antibody neutralization therapy include infectious agents and their toxins, such as tetanus toxin, anthrax toxin, botulinum toxin, and lipid A. The peripheral blood of patients infected with bacteria, fungi, protozoa or viruses typically contains circulating antibody-producing cells that can be isolated and fused with Karyochi cells to make Karyochi-based hybridomas that produce fully human monoclonal antibodies against antigens that are specifically produced in the infected host, including those produced in response to infection, or antigens expressed by the infectious agents themselves, for example bacterial endotoxins. As an example, PBLs can be obtained from patients with septic shock, Aids, Hanta virus infection, HIV, HTLV-I, HTLV-II, influenza, Ebola virus, human papilloma virus, *Staphlococcus, Streptococcus, Klebsiella, E. coli*, anthrax or *cryptococcus*, Hepatitis B and C, or herpes virus. Karyochi-based hybridomas made by fusing these PBLs (or other antibody-producing cell) with Karyochi cells can be screened against the respective antigens to select hybridomas that make monoclonal antibodies with therapeutic value and specificity. Using the cells and methods of the present invention bulk quantities of anti-HIV antibodies for use in passive immunotherapy for treating AIDS can be made. Such antibodies can be used in an autologous or heterologous manner. Therefore another embodiment of the invention is directed to human Karyochi-based hybridomas made by fusing a lymphoid cell from a patient having an infection, disease, or condition to a Karyochi fusion partner cell, and to the HuMAbs they produce that are specific for an antigen associated with the respective infection, disease or condition. The antigen can be specific for the pathogen causing the infection, or it can bind to a protein made by the pathogen, or to an antigen made by the infected host according to pathogen DNA. The antigen can also be directed to cytokines and lymphokines that are produced in abnormal amounts in an infected individual.

Human monoclonal antibodies can also be used therapeutically to treat patients having an autoimmune disease by using them to block autoantibodies, or to block the patient's own $CD4^+$ T cells which are involved in autoimmune cellular cytotoxicity. In one embodiment of the invention, human monoclonal antibodies against $CD4^+$ cells can be generated by Karyochi-based hybridomas made by fusing a Karyochi cell with a patient's $CD4^+$ cell. The resulting hybridomas will then be screened for the production and secretion of HuMAbs directed to CD4. These HuMAbs can be administered therapeutically to reduce or deplete the patient's excess $CD4^+$ cells, thereby relieving autoimmune cellular attack. The antibodies can also be used in other patients suffering from overexpression of CD4 because the antibodies are fully human and should be well tolerated. In another embodiment, Karyochi cells can be used to generate Karyochi-based hybridoma cells capable of producing anti-idiotypic HuMAbs directed to specific autoantibodies. For example, autoimmune thyroiditis is an autoimmune dysfunction in which there is a high titer of anti-thyroglobulin antibodies in a patient's plasma. PBL-derived lymphocytes can be isolated from such patients for fusion with Karyochi cells. The resultant Karyochi-based hybridoma cells can be screened to identify those capable of producing HuMAbs with a substantial anti-idiotypic immune response directed against the autoantibodies reactive with thyroglobulin. These anti-idiotypic antibodies can then be used to modulate the autoimmune disease by neutralizing and thereby reducing or depleting the anti-thyroglobulin antibodies in the patient. Such an approach may be used autologously or heterologously. In an autologous approach, the anti-idiotypic antibody-producing cells are identified in peripheral blood of the patient to be treated, then isolated and fused with Karyochi cells. Following selection for specific anti-anti-thyroglobulin HuMAbs antibodies produced by Karyochi-based hybridomas, the antibodies are passively administered to the original patient. In a heterologous approach, the anti-anti-thyroglobulin antibodies are administered to a different patient.

HuMAbs produced by Karyochi-based hybridomas can be used in prevention of organ transplant rejection by blocking T cells through the OKT-3 (anti-CD3) marker. Antibodies to adhesion molecules (anti-integrin antibodies) can also be made that prevent migration of immune cells, which is important, for example in rheumatoid arthritis. Blood clotting may be modulated, for example, in acute cardiac ischemia following coronary angioplasty, using human monoclonal antibodies against GPIIb/IIa of platelet. Intravenous infusion of immunoglobulins helps to neutralize the Fc-receptor mediated cell aggregation of platelet or other blood cells (e.g. thromobytopenic purpura). Hu-MAbs may be also be used to detoxify or neutralize toxin or venom exposure. Such exposures include, but are not limited to snake, spider or poison toad bites, and yellow jacket or scorpion stings. To do this, lymphoid cells are isolated from a patient exposed to the toxin/venom and these cells are fused with Karyochi cells to make Karyochi-based hybridomas, the Hu-MAbs of which are screened for affinity for the toxin/venom. Alternatively, lymphocytes can be immunized with the toxin/antigen at non-toxic doses in vitro as is described below, and these cells can be used for fusion. There is a shortage of natural human immunoglobulin required for these kinds of treatments. The horse anti-serum currently used to neutralize rattlesnake venom causes serum sickness disease in 30% of cases. The human monoclonal antibody production system described herein facilitates in vitro production of essentially unlimited quantities of fully human immunoglobulins that can be selected to fit particular needs. For example, in the case of immunoglobulin which blocks Fc receptors, instead of treating the patient with the pooled preparation of immunoglobulins where only a small fraction of molecules possess the required qualities, the immunoglobulin preparation of the molecules with the required properties can be produced using Karyochi fusion partners and Karyochi-based hybridomas.

Previous attempts to generate human anti-tumor antibodies or antibodies against infectious agents required forced or artificial immunization of a subject with purified or isolated antigen. Using the Karyochi cells and hybridomas of the present invention, the antigen may be unknown. The starting material for developing antibodies is the pool of immunocompetent lymphocytes which evolved as a part of natural immune response to the foreign antigens presented in its natural form and environment in vivo. Lymphocytes to be used in forming Karyochi-based hybridomas can be immunized in vitro against antigens of interest as was described in Trakht, U.S. Pat. No. 6,197,582. Hybridomas can then be selected for their ability to make HuMAbs against the antigens using procedures well known in the art. Basically, freshly isolated lymphocytes will be resuspended in the appropriate culture medium such as RPMI-S-containing 2.5 mM L-leucine methyl ester (Leu-OMe) (Borrebaeck, C A K, et al., 1987), and cultured to a final concentration of about $10^7$ cells per ml. The suspended lymphocytes can then be incubated with a mitogen such as pokeweed mitogen (PWM) and the antigen of interest in different concentrations. After immunization the immunized lymphocytes can be fused with Karyochi cells to make Karyochi-based hybridomas. Assays such as enzyme-linked immunoassay (ELISA) can be used to test Karyochi-based hybridoma supernatants for the presence of antibodies against the antigens of interest.

Therefore, in certain embodiments, the human antibody-producing lymphoid cell to be fused with the Karyochi cells of the present invention is obtained from a patient having a condition such as a disease condition (hereafter "the condition") for which at least one antigen associated with the condition is produced. This antigen can be one that has been identified and is known, or an unknown antigen that causes host lymphocytes to make antibodies against it. Another embodiment is directed to a human Karyochi-based hybridomas made by fusing a lymphoid cell taken from a patient having the condition with a Karyochi cell, such that the resulting Karyochi-based hybridoma secretes a human monoclonal antibody having specific or high binding affinity for the disease-specific antigen. Other embodiments of this invention are directed to the HuMAbs produced by the Karyochi-base hybridomas and their therapeutic use, and to any other monoclonal antibodies made by any species of Karyochi hybridoma. According to another embodiment of this invention, the disease-specific antigen is a tumor-associated antigen, a cell-specific antigen, a tissue-specific antigen, an enzyme, a nucleic acid, an immunoglobulin, a toxin, a viral antigen, a bacterial antigen or a eukaryotic antigen. In an embodiment of this invention, the antigen is a mammalian, insect, E. coli or Klebsiella antigen. In some embodiments, the HuMAbs made by the Karyochi-based hybridomas are coupled to an effector compound such as a cytotoxic agent, drug, enzyme, dye or radioisotope to be used therapeutically or diagnostically.

The mechanisms underlying the stable production of HuMAbs produced by human Karyochi-based hybridomas are unknown. It has been suggested by others that human chromosomes or their fragments retained in the partner line after the first fusion modify the intracellular environment in such a way that the human lymphocyte chromosomes or fragments after the second fusion are stabilized. Oestberg L, and Pursch E., 1983. The fully human Karyochi cells of the present invention are a significant improvement over previous fusion partner cell lines because they can be used to make Karyochi-based hybridomas that produce fully human monoclonal antibodies, and because Karyochi cells compare favorably to MFP2 cells as fusion partners in other parameters. The fully human Karyochi cells and the Karyochi-based hybridomas of the present invention include provide the basis for studying various repertoires of natural human antibodies under normal and pathophysiological conditions. The cells and methods described herein provide the basis to identify novel tumor or infectious disease-associated markers, and provide fully human monoclonal antibodies for in vivo therapeutic and in vitro diagnostic use with insignificant risk of side effects even with multiple administrations. According to an embodiment of this invention, the HuMABs are coupled to a detectable marker such as a radiolabeled molecule, a fluorescent molecule, an enzyme, a ligand, a calorimetric marker or a magnetic bead for easy detection.

The present invention also provides an isolated nucleic acid encoding the human monoclonal antibody produced by the described human Karyochi-based hybridomas. The nucleic acid may include, but is not limited to DNA, RNA, cDNA, oligonucleotide analogs, vectors, expression vectors or probes. Additionally, the present invention contemplates a DNA construct for expressing the nucleic acid encoding the monoclonal antibody in a host cell capable of expressing the monoclonal antibody or portions thereof.

There has long been a need for human monoclonal antibodies for diagnosis, treatment, and monitoring of various conditions including diseases such as cancer. Attempts to employ xenoantibodies in clinical trials have not produced promising results. Non-human antibodies from mice, for example, cause development of a human anti-mouse immune response, sensitization to foreign protein which may eventually result in anaphylactic reaction, and lack of biological effect since the effector properties of the xenoantibodies may mismatch the components of the human immune system. Human monoclonal antibodies have numerous advantages. One is that human monoclonal antibodies can identify those tumor-associated antigens (TAA) which are immunogenic only in humans, while xenoantibodies in most cases recognize those antigens and antigenic epitopes which express immunodominance in a host and are often the tissue specific epitopes. Another advantage is the well-developed interaction of human monoclonal antibodies with the effector components (such as complement) of the host immune system. In addition, allergic and/or anaphylactic reaction to the injectible human monoclonal antibodies is less of a concern since human monoclonal antibodies are syngenic in human subjects. The Karyochi cells fusion partner cell lines, Karyochi-based hybridomas and HuMAbs of the present invention facilitate the identification, immortalization, and ex-vivo expansion of fully human monoclonal antibody-producing cells that emerge in vivo from natural humoral immune responses to an antigen. Since the human lymphoid cells used to make the human Karyochi-based hybridomas are a part of the natural immune system response, the fully human monoclonal antibodies they produce are compatible with other components of the immune system, and are able to induce a safe, effective and specific biological response in a human subject.

As described above, specific monoclonal antibody-producing cells are identified and may be produced in unrestricted fashion, ex-vivo (using bioreactors, SCID mice, etc). The antibodies may be used therapeutically as passive immunotherapy either autologously in the same subject or heterologously in a different subject. Syngenic or allogenic use of human monoclonal antibody can be highly effective since the same patient can be infused with fully HuMAbs many times without the risk of developing an anti-xenogenic immune response. The infused HuMAbs, depending on their effector functions, can initialize complement dependent cytolysis of the target tumor cells, or antibody-dependent cellular cytotoxicity antibody dependent cellular cytotoxicity (ADCC) (by NK or CTL cells), or provide direct cytotoxic effect through apoptosis. The developed antibodies may also be applied both to invasive diagnostics (imaging, immunoscintigraphy) or therapy (drug targeting, radioimmunotherapy, complement-dependent cytolysis, ADCC, apoptotic cytolysis etc.)

Native antibodies and immunoglobulins, which include human monoclonal antibodies produced by Karyochi hybridomas, are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. At one end of each heavy chain there is a variable domain (VH) that is followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains. Chothia et al. J. Mol. Biol. 186:651 (1985); Novotny and Haber, Proc. Natl. Acad. Sci. U.S.A. 82:4592 (1985); Chothia et al., Nature 342:877-883 (1989).

Monoclonal antibodies or portions thereof, include "F(ab')$_2$" and "Fab" fragments that are produced by treating monoclonal antibody with a protease such as pepsin and papain. "F(ab')$_2$" and "Fab" fragments means an antibody fragment generated by digesting immunoglobulin near the disulfide bonds in the hinge regions existing between each of the two H chains. For example, papain cleaves IgG upstream of the disulfide bonds in the hinge regions existing between each of the two H chains to generate two homologous antibody fragments. Each of these two homologous antibody fragments is called Fab'. In another example, pepsin cleaves IgG downstream of the disulfide bonds in the hinge regions existing between each of the two H chains to generate an antibody fragment slightly larger than the fragment in which the two above-mentioned Fab' are connected at the hinge region. This antibody fragment is called F(ab')$_2$.

An "isolated" monoclonal antibody within the scope of the present invention is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In certain preferred embodiments, the monoclonal antibody will be purified (1) to greater than 95% by weight of antibody as determined by the Lowry method, and terminal or internal amino acid sequence by use of a spinning cup sequenator, or (2) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The Karyochi-based hybridomas producing monoclonal antibodies can be screened by cultivating the cells in microtiter plates, for example, and by measuring the reactivity of the culture supernatant in the well in which hybridoma growth is observed, to any antigen of interest including an immunogen, for example, by enzyme immunoassay such as radio immunoassay (RIA) and enzyme-linked immuno-solvent assay (ELISA). The monoclonal antibodies can be produced from Karyochi-based hybridomas by cultivating the hybridomas in vitro or in vivo such as in the ascites fluid of a mouse, rat, guinea pig, hamster, or rabbit, preferably a rat or more preferably a mouse, and isolating the antibodies from the resulting culture supernatant or ascites fluid. For example, in the ascites transudate method, a mineral oil such as pristane (2,6,10,14-tetramethylpentadecane) is administered by i.p. to the mammal in which the hybridoma is to be grown, for example, the mammal can be the same species from which the myeloma cells were derived. Then, the hybridoma, from about $1 \times 10^7$ to $1 \times 10^9$ cells, are administrated i.p. to the animal, and a large amount of hybridoma cells are grown in the animal. After 1 to 4 weeks, preferably 2 to 3 weeks, ascites fluid or serum is collected from the animal. If it is necessary to purify the antibody from the ascites fluid or serum, it can be purified by conventional methods such as salting-out with ammonium sulfate, ion-exchange chromatography on anion exchanger e.g. DEAE cellulose, affinity chromatography on Protein A sepharose and gel filtration, and these may be used singly or in combination. Other methods for growing hybridomas and isolating monoclonal antibodies are described in U.S. Pat. No. 6,605,705 that is incorporated by reference herein.

Cultivating the Karyochi-based hybridomas in vitro can be performed depending on, e.g., the property of cells to be cultured, the object of a test study, and the various conditions of a cultivating method, by using known nutrient media or any nutrient media derived from known basal media for growing, maintaining, and storing the hybridomas to produce monoclonal antibodies in culture supernatant. Monoclonal antibodies can be isolated and purified from the hybridoma culture supernatant or ascites fluid mentioned above by any method known in the art, including, saturated ammonium sulfate precipitation, euglobulin precipitation method, caproic acid method, caprylic acid method, ion exchange chromatography (DEAE or DE52), affinity chromatography using anti-immunoglobulin column, or protein A column. Human monoclonal antibodies of the present invention can also be isolated using conventional methods such as cell culture method, ascites transudate method, etc. For example, in the cell culture method, the hybridoma is cultured for 2 to 14 days in a medium such as RPMI-1640, MEM, or E-RDF containing 10 to 20% calf serum or in a serum-free medium under conventional culture conditions, e.g. 37 degrees Centigrade, 5% $CO_2$. The antibody can then be obtained from the culture.

"Binding rate constant (Ka)" herein means a value indicating the binding strength (degree) of the monoclonal antibody to the target antigen calculated based on the antibody antigen reaction kinetics. "Dissociation rate constant (Kd)" means a value indicating the dissociation strength (degree) of the monoclonal antibody from the target antigen. "Dissociation constant (Kd)" is a value obtained by dividing the "dissociation rate constant (Kd)" by the "binding rate constant (Ka)" value. These constants are used to represent the affinity of the monoclonal antibody to antigen and its activity to neutralize antigen. The constants can be analyzed according to various methods, and can be easily analyzed using a commercial assay kit BiacoreX (Amersham Pharmacia) or a similar kit according to the manual and experimental method attached to the kit. ka, kd and Kd values obtained using the kit are expressed in 1/M·Sec, 1/Sec and M (mol) units, respectively. Higher ka values indicate stronger antigen binding activity of monoclonal antibody tested, and smaller Kd values show stronger antigen neutralizing activity of antibody.

The invention has been described in the foregoing specification with reference to specific embodiments. It will however be evident that various modifications and changes may be made to the embodiments without departing from the broader spirit and scope of the invention. The specification and drawings are to be regarded in an illustrative rather than a restrictive sense.

EXAMPLES

Example 1

Preparing Human Chimeric Karyochi Cells

Donor Nucleus Isolation for IINI

A digitonin-based protocol was used to isolate nuclei as described previously. Briefly, cells in monolayer were rinsed twice with ice-cold cell washing buffer (CWB) composed of 5 mM Tris-HCl, pH 7.4, 50 mM KCl, 0.5 mM EDTA, 0.05 mM spermine, 0.125 mM spermidine, 0.5% thioglycol, and 0.25 mM PMSF. The cells were then scraped off with a plastic cell lifter (Fisher Scientific, Springfield, N.J., USA) after CWB containing 0.1% digitonin (water-soluble form; Sigma) was placed on the monolayer (5 mL per 15 cm plate). The cell suspension was forced three times through a 21-gauge hypodermic needle and layered over 2 mL of 12.5% glycerol in CWB-digitonin in a 15-mL conical plastic tube. Nuclei were pelleted by centrifugation at 3000 g for 10 min. This nuclei isolation protocol was used to prepare the nuclei for IINI.

Isolation of Lymphocytes: Splenocytes, Lymph Cells and PBLs

Lymph Node:
Media: Any serum-free media supplemented with Sodium Pyruvate, non-essential amino acids and vitamins can be used to isolate human lymphocytes. Lymph node tissue was placed in 100 mm Petri dish, dissected with scissors, and then pushed through a sieve with glass pestle. The pellets were suspended in DMEM medium, with 0.5% Fetal Calf Serum and the cell suspension is transferred to 50 ml tube, underlayed with Histopaque-1.077 (Sigma, H8889), (⅓ of the volume of cell suspension) and centrifuged at 400 g room temperature (RT) fir 40 minutes. Lymphocytes form an opalescent ring on the border of the Hystopaque that facilitates their identification for aspiration. The lymphocytes are then aspirated, washed twice with the same media and counted.

Blood:

Blood is diluted 1:1 with any serum-free media supplemented with Sodium Pyruvate, non-essential amino acids and vitamins, and dispensed over 50 ml tubes. Histopaque-1.077 (Sigma, H8889) is underlayed (⅓ of the volume of cell suspension) and centrifuged at 400 g room temperature for 40 minutes. Peripheral blood lymphocytes form an opalescent ring on the border of the Hystopaque that facilitates their identification for aspiration. The PBLs are then aspirated, washed twice with the same media and counted.

B. Preparation of Karyochi

FP0 cells were established in culture from a biopsy taken from a Hodgkin's lymphoma patient. The FPO cells have a mixed phenotype indicating their T-cell origin: $CD3^+CD4^+CD19^-CD20^-CD45^-CD38^-CD33^-CD34^-CD138^-\lambda^-\kappa^-$.

The cells have an irregular shaped morphology, and they grow in clumps in suspension. These cells were mutagenized by ultraviolet light in several rounds of 30 seconds each, and selected for 8-Azaguanine (8-Ag) resistance by gradually increasing the 8-Ag concentration from 5 ug/ml to 20 ug/ml. The final mutant FP0-AgR cells were able to grow in the presence of 20 ug/ml of 8-Ag. These FP0AgR cells were sensitive to HAT (Hypoxanthine, Aminopurine, and Thymidine) such that all cells died in the presence of HAT within 72 hours. FP0-AgR cells were then transfected with $Neo^+$ plasmid, and Geneticin G418-resistant clones were selected in the presence of 1,000 ug/ml of G418 (total mass concentration with effective concentration around 600 ug/ml). The resulting FP0-AgR-neo$^+$ cells were used as nuclei donors.

Human FP1.0 cells were established in culture from a biopsy taken from a myeloma patient. The cells were adopted in culture and grew in the presence of 10% FCS (fetal calf serum). These cells were not mutagenized and the original "wild" type was used as the recipient cell to create a karyotypic chimera. FP1.0 cells were subjected to phenotyping and found to have the following phenotype: $CD38^+CD56^+CD138^+CD45^-CD19^-CD20^-CD3^-CD4^-CD10^+CD33^-CD34^-\lambda^-\kappa^-$. The cells have a round shape; and they grow in suspension reaching densities close to $2\times10^6$ cells/ml in standard RPMI-1640 media supplemented with vitamins, glutamine, non-essential amino acids and 10% FCS.

Karyochi (KARYOtypic CHImeras) cells were generated by removing the nucleus from an FP0-AgR-neo+ cell such that the nucleus is substantially free of cytoplasm. The isolated FP0 nucleus is the donor nucleus. The donor nucleus is transferred into the cytoplasm of recipient FP1.0 cells where it ultimately fuses with the nucleus of the FP1.0 cell to form the Karyochi cell. Donor nucleus transfer can be accomplished using two different techniques. Intracytosolic injection of donor nucleus into recipient cell cytosol is the preferred method for nuclear transfer. (Intra Cytosolic Nucleus Injection—ICNI). This method involves removing the nucleus from the donor cell using ultra thin micromanipulator needle (diameter<6 um) and injecting the nucleus into the cytoplasm of the recipient cell.

One of the cell fusion methods we used is a variation of the impact-induced administration of donor nucleus into the recipient cell cytoplasm. Impact-induced administration of donor nucleus into the recipient cell cytoplasm (Impact-Induced Nucleus Administration—IINA) uses the preparation of purified nuclei isolated from donor cells that are pelleted onto a bed of recipient cells under the several hundreds of G-force using a centrifuge. The relevant references are: Hahn C. et al., 1990; Smith P. et al., 1988; Hill M. et al., 1985, Nahava K. et al., 1977; and Jett M. et al. 1977, these references are incorporated by reference herein. When a force of between 400-500 g is applied, a certain fraction of nuclei penetrate the recipient cell membrane and integrate with the cell cytoplasm preserving their intactness and functionality. Dikaryons typically survive well, while cells with three and more nuclei die. Karyotyping the cells to determine the number of chromosomes then is done to positively identify Karyochi cells that received two nuclei.

Both methods result in a dikaryon, which is a cell carrying two nuclei, one is the recipient's original nucleus and another one is the donor nucleus. During the metaphase of the first mitotic division following the nucleus transfer, the nuclei fuse and the chromosomes from both nuclei mix. After the recipient cell divides, the resulting daughter cells will carry the mixed karyotype consisting of chromosomes of both parental cells in a single nucleus. To select the true chimeras (heteromyelomas) the cells were incubated for 48 hours after which time they were put in media with the selective agents HAT and G418. Only true chimeras called Karyochi cells could live on this selective medium. The cells that did not receive the donor nucleus die in the presence of HAT. Similarly, cells that received the donor nucleus but for some reason lost their own nucleus will also die in the presence of G418. Only Karyochi cells can live in the presence of HAT and G418.

C. The Karyochi-7 Adoptive Fusion Protocol

The protocol for fusion of Karyochi Cells (Karyochi-7) with Lymphocytes isolated from Spleen, Lymph Node or Blood to make Karyochi-based hybridomas is set forth below:

1. Both lymphocytes and Karyochi-7 cells need to be washed 4 times by centrifugation at 200 g, RT for 10 min. and counted prior to fusion. Media suitable for washing include any serum-free media supplemented with L-glutamine, Na Pyruvate, NEAA and Vitamins.

2. Cells are counted using a hemacytometer in a presence of Trypan Blue (Cellgro, 25-900-LI) to determine cell viability. Trypan blue is supplied as stock solution 0.4%. To prepare 0.1% working solution, mix 1 part Trypan Blue and 3 parts of PBS. To count the cells, mix equal volumes of cell suspension and 0.1% Trypan Blue.

3. After the cells are counted, mix Karyochi-7 and lymphocytes at a ratio 1:4 or 1:5 (Karyochi-7:lymphocytes), add washing media up to 50 ml and pellet the cell mixture at 200 g, RT for 10 min.

4. Decant the supernatant and leave the tube upside down for 30 sec. Aspirate all the remaining media.

5. Resuspend the pellet by shaking the tube with the thumb.

6. Add pre-warmed at 37° C. Polyethylene glycol (PEG-1500) (Sigma, P7181), 300 ul for a cell mixture of about $10\text{-}300\times10^6$ cells, and 400 ul for a cell number above $300\times10^6$. Incubate with constant shaking for 3 min. at room temperature (RT).

7. Wash out the PEG solution with washing media using the following schedule: 10 ml for 10 minutes, and 5 ml for 5 minutes.

8. Continue washing with the PEG washing procedure by adding C-RPMI:—10 ml for 5 minutes, and 5 ml for 1 minute.

9. Centrifuge the cell suspension at 200 g at RT for 10 min. Resuspend the cells in C-RPMI, containing 1×HAT (Sigma, H0262) and 1× HT (Sigma, H0137) at a concentration $1\times10^6$ lymphocytes/ml and spread the suspension over 96 well plates in an amount of about 200 ul/well (Falcon, 3872).

10. Change ½ of the media with the same medium containing HAT and HT every 3-4 days. Let the Karyochi-based hybridoma cells grow for about 2-4 weeks prior to screening. Screening should begin when the Karyochi-based hybridoma cells occupy approx. ⅓ of the volume of the well.

D. Cloning of Karyochi-Based Hybridoma Cells

Karyochi-based hybridoma cells are cloned by limiting dilutions using Hybridoma Cloning Factor (Origen, 50-0615) as a feeder (20% in C-RPMI). Cloning takes 2-4 weeks depending on the cells.

E. Screening Karyochi-Based Hybridoma Supernatant for the Presence of Nonspecific Ig Secretion.

The screening method for detecting the presence of nonspecific immunoglobulin secretion is set forth below:

1. Prepare carbonate-bicarbonate buffer (0.1 M $Na_2CO_3$, 1 part, 0.1 M $NaHCO_3$, 9 parts), pH 9.6.
2. Capturing antibodies Goat-Anti-Human IgG (Fc-specific) (Sigma, 12136) or Goat-Anti-Human IgM (Sigma, 12386) were used.
3. Prepare a capturing antibody solution of 1 ug/ml carbonate-bicarbonate buffer and spread it over a 96 well plate (non sterile, Nunc, 439454) using 100 ul/well (100 ng/well). Cover the plate with parafilm and incubate overnight at +4° C.
4. Wash the plate out 5 times with deionized (DI) water and block nonspecific binding with 0.3% dry milk (Foodclub) in Phosphate buffered saline (PBS) for 1 hr at RT.
5. Apply the Karyochi-based hybridoma supernatants in an amount of 100 ul/well. Apply standard Human IgM (Sigma I8260) or standard Human IgG (Sigma 12511) in an amount of 5 ug/well, the highest concentration and incubate 2 hrs at RT.
6. Wash the plate 6 times with DI water.
7. Prepare a solution of secondary antibodies (Goat-Anti-Human polyvalent Ig's-Peroxidase labeled, Sigma, A8400) 1:2000 in PBS/milk (0.3%). Apply 100 ul of labeled antibodies to the plate and incubate 1 hr at RT.
8. Wash the plate 8 times with DI water.
9. Dissolve 1 tablet of substrate (Tetramethylbenzidine, Sigma T5525) in 1 ml DMSO and add 9 ml of 0.05 phosphate-citrate buffer, pH 5.0 (Sigma P4809) containing 0.03% sodium perborate (Sigma P4922).
10. Add substrate solution to the wells (100 ul/well).
11. Read the plate at 655 nm (filter #7).
12. The isotype of the secreted monoclonal antibodies can be determined by ELISA using murine anti-human light and heavy chains (MAH-L, H) and goat anti-mouse immunoglobulin (25 ug/ml) conjugated to peroxidase and absorbed with human immunoglobulin. Production of cytoplasmic light and/or heavy chains in Karyochi-based hybridomas, can be estimated immunocytochemically using the peroxidase-anti-peroxidase system (PAP) as described in U.S. Pat. No. 6,197,582, the entire contents of which is hereby incorporated by reference as if set forth fully herein.

F. Fusion Protocols

Fusion protocols were used in accordance with those described for the respective cell lines. In those cases when such protocols were not available, the Karyochi-7 adopted fusion protocol was used. The following parameters were monitored over time during the course of each experiment:
fusion efficiency, expressed as number of wells showing positive cell growth and frequency of hybrids per number of human lymphocytes;
number of wells showing Ig production;
stability of Ig production in non-cloned Karyochi-based hybridoma populations over the 6 week period;
clonogenicity; and
stability of Ig production in individual clones over a period of at least 6 weeks.

G. Chromosomal Analysis

Preparations of metaphase chromosomes can be obtained by the following technique. Adding colchicine to cells during exponential growth. Cells were then trypsinized and stained for G-banding as described (Seabright S., Lancet 1971; 2:971.) (10-15 plates from each line). To count chromosome number, at least 50 metaphase figures are then analyzed for each cell line.

H. DNA Analysis by Flow Cytometry

To estimate the DNA content the cells ($1.times.10.sup.6$) can be fixed with 1 ml 70% ethanol, washed, incubated for 2-3 hours with 0.3 mg/ml Ribonuclease A (Serva) in Hank's solution (pH 7.4) and stained for 2 hours with propidium iodide (0.05 mg/ml, Sigma) in Hank's solution. The DNA content is then measured in a FACS-II cytofluorometer (Becton Dickinson). Fluorescence was excited by an argon ion laser at 488 nm (164-05 Model, Spectra-Physics) at a power of 400 mW and registered behind a 600 nm long pass interference filter (Ditric Optica).

REFERENCES

Antonov A S, et al., Atherosclerosis 1986; 59:1.
Appels R, Bell P B, Ringertz N R.
Borrebaeck C A K, et al., Biochem. Biophys. Res. Commun. 1987; 148:941.
Birch-Machin I., et al. J. Virol. Methods. 2000; 88(1): 89-104.
Brodin T, J. Immunol. Meth. 1983; 60:1.
Casual O, Science 1986; 234:476.
Dijkwel, P. A., Vaughn, J. P., Hamlin, J. L., *Mol. Cell Biol.* 1991, 11, 3850-3859.
Fazekas de St. Groth, S., et al. Journal of Immunological Methods 35: 1-21 (1980).
Friedman H, Klein T W, Nakano M, Nowotny A, and Eds. Advances in Galanos G, et al., Eur. J. Biochem 1969; 9:245.
Glassy M C, Proc. Natl. Acad. Sci (USA) 1983; 80:6327.
Goldman-Leikin R E, J. Lab. Clin. Med. 1989: 113:335.
Hahn C G, Covault J. Anal Biochem. 1990, 190(2):193-7.
Hill M, Hillova J, Mariage-Samson R, Marx M. Exp Cell Res. 1985, 156(1):127-39.
Hlinka D, et al, Hum Reprod. 1998 July; 13(7):1922-7.
Hodge, Deborah L., et al., Molecular and Cellular Biology, 2002, p. 1742-1753, Vol. 22, No. 6.
Isaacson C, et al., Clin Chem. 1988 September; 34(9):1681-8.
Jeon K W. Protozool. 1975 August; 22(3):402-5.
Jett M, Seed T M, Jamieson G A. J Biol Chem. 1977, 252(6): 2134-42.
Kalantarov G, Rudchenko S, Trakht I. Human Antibodies, 11, 3, 2002, pp. 85-96.
Katayose H, et al., Theriogenology. 1999 November; 52(7): 1215-24.
Khalili M A, et al., J Assist Reprod. Genet. 2002; 19: 84-6.
Kohler G, and Milstein C., Nature 1975; 256:495
Kozbor D, et. al., J. Immunology 1984; 133:3001.
Kozbor D, and Roder J., J. Immunology 1981; 127:1275.
Kyriacou K. I, Hum Reprod. 1995 April; 10(4):880-2.
Levy, R., and Miller R A. Federation Proceedings 1983; 42:2650.
Moller, G, 1995. (editor) Immunological Reviews Vol 145: Tumor Immunology
Nakaya K, et al. Cancer Res. 1977, 37(10):3701-6.
Nilsson K. and Ponten J., Int. J. Cancer 1975; 15:321.
Nilsson K, et al. Nature. 1983 Apr. 14; 302(5909):629-30.

Nusser K. D., et al., Human Reproduction, Vol. 16, No. 1, 130-137.
Oestberg L, and Pursch E., Hybridoma 1983; 2:361.
Ostberg L., Transplant Proc. 1992 August; 24(4 Suppl 2):26-30.
Ostberg L, Methods Enzymol. 1986; 121:228-34.
Ollson L, et al., J. Immunol. Methods 1983; 61:17.
Posner M R, et al., Hybridoma 1983; 2:369.
Reading C L., J. Immunol. Meth. 1982; 53:261.
Raison R L, et al., J. Exp. Medicine 1982; 156:1380.
Rokhlin O V, 8th Int. Congress of Immunology, Berlin. Abstracts 1989; 6.
Seabright S., Lancet 1971; 2:971.
Shnyra A A, et al., In: Exp. Medicine & Biology Endotoxin New York: Plenum, 1990; 256:681.
Smith P J, Friede M H, Scott B J, von Holt C. Anal Biochem. 1988, 169(2):390-4.
Sugasawara, R., Bio/Technology 6: 895-902 (1988).
Sugasawara, R., Journal of Tissue Culture Methods 12: 93-95, (1989).
Teng N N H, Proc. Natl. Acad. Sci. (USA) 1983; 80:7308.
Trokoudes K M, et al. J Cell Biol. 1975 October; 67(1):174-88.
Weiss M C, and Green H. Proc. Natl. Acad. Sci. (USA) 1967; 58:1104.
Zimmerman U., et al. Hum. Antibodies Hybridomas 1995; 6(2):77-80

What is claimed is:

1. The human lymphoma cell line FP0 having ATCC Patent Deposit Designation Number PTA-7466.

2. The human myeloma cell line FP1.0 having ATCC Patent Deposit Designation Number PTA-7465.

3. The human fusion partner cell line Karyochi-7 having ATCC Patent Deposit Designation Number PTA-7467.

4. The human fusion partner cell line Karyochi-XX having ATCC Patent Deposit Designation Number PTA-7468.

5. A method for making a Karyochi fusion partner cell line using cells from a single animal species, comprising
    a. isolating a donor nucleus that is substantially free of cytoplasm from either a first malignant B-lymphocyte cell line or a normal B-lymphocyte in the single animal species,
    b. transferring the donor nucleus into the cytoplasm of a recipient cell from a second T- or B-lymphoid cell line in the single animal species,
    c. allowing time for the synchronization and fusion of the two nuclei in the recipient cell, and
    d. identifying and selecting the Karyochi fusion partner cell line.

6. The method of claim 5, wherein the donor nucleus is transferred to the recipient cell cytoplasm by intra-cytosolic nucleus injection.

7. The method of claim 5, wherein the donor nucleus is transferred to the recipient cell cytoplasm by impact induced nucleus administration.

8. The method of claim 5, wherein the first and second human lymphoid cell lines are different human cell lines selected from the group comprising myeloma, lymphoma, multiple myeloma, lymphoblastoma and leukemia cell lines.

9. The method of claim 5, wherein the animal species is a member of the genus mammals.

10. The method of claim 9, wherein the mammal is a human.

11. The method of claim 5, wherein the donor cell comes from the human lymphoma cell line FP0 having ATCC Patent Deposit Designation Number PTA-7466, and the recipient cell comes from the human myeloma cell line FP1.0 having Patent Deposit Designation Number PTA-7465.

12. The method of claim 5, wherein the donor nucleus and the recipient cell each express a different selection marker that is a member selected from the group comprising 8-Aza-guanine resistance, 5-Bromouracil, 5-Fluorouracil or G418 resistance.

13. A method for making a monoclonal antibody-secreting Karyochi-based hybridoma using cells from a single animal species, comprising
    a. obtaining a Karyochi fusion partner cell that is made by:
        1. isolating a donor nucleus that is substantially free of cytoplasm from either a first malignant B-lymphocyte cell line or a normal B-lymphocyte from the single animal species,
        2. transferring the donor nucleus into the cytoplasm of a recipient cell from a second T- or B-lymphoid cell line from the single animal species,
        3. allowing time for the synchronization and fusion of the two nuclei in the recipient cell to form the Karyochi fusion partner cell, and
        4. identifying and selecting the Karyochi fusion partner cell line,
    b. fusing the Karyochi fusion partner cell of step (a) with an antibody-producing B lymphoid cell from the single animal species,
    c. allowing time for the nucleus of the Karyochi cell and the nucleus of the B lymphoid cell to synchronize and fuse,
    d. incubating the fused cell formed in step c. under conditions permissive to the production of antibody, and
    e. identifying and selecting the monoclonal antibody-secreting Karyochi-based hybridoma.

14. The method of claim 13, wherein the single animal species is a species of mammal.

15. The method of claim 14, wherein the mammal is a human.

16. The method of claim 13, wherein the single animal species is a non-human mammal, reptile or bird.

17. The method of claim 13, wherein the antibody-producing B lymphoid cell of step b. is a human B cell that is isolated from a member of the group comprising spleen, lymph node, and blood.

18. The method of claim 13, wherein the animal is human, the antibody-producing B lymphoid cell of step b. comes from a human having a condition that causes the expression of an antigen associated with the condition, and the Karyochi-based hybridoma produces human monoclonal antibodies that are specific or have high affinity for the antigen.

19. The method of claim 18, wherein the condition is a disease, and the antigen associated with the condition is a disease-specific antigen that elicits an immune response.

20. The method of claim 19, wherein the disease is a member of the group comprising cancer, an infectious disease, an autoimmune disease, a disease associated with over-expression of hormones or enzymes, graft vs. host disease, and cardiovascular disease.

21. The method of claim 18, wherein the antigen is a member selected from the group comprising a tumor-associated antigen, a cell specific antigen, a tissue-specific antigen, an enzyme, a hormone, a nucleic acid, a toxin, a viral antigen, a bacterial antigen, a fungal antigen, a parasitic antigen, a pyron, and a eukaryotic antigen.

* * * * *